US006794496B2

(12) United States Patent
Ghoshal et al.

(10) Patent No.: US 6,794,496 B2
(45) Date of Patent: Sep. 21, 2004

(54) IMMUNOASSAY FOR LSD AND 2-OXO-3-HYDROXY-LSD

(75) Inventors: Mitali Ghoshal, Noblesville, IN (US); Stephen Vitone, Noblesville, IN (US); Gerald F. Sigler, Carmel, IN (US); Alan J. McNally, Carmel, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 288 days.

(21) Appl. No.: 09/733,534

(22) Filed: Dec. 8, 2000

(65) Prior Publication Data

US 2001/0044118 A1 Nov. 22, 2001

Related U.S. Application Data

(60) Provisional application No. 60/196,030, filed on Apr. 7, 2000.

(51) Int. Cl.$^7$ ..................... C07K 17/06; C07D 519/02; C12N 9/96; G01N 33/533; G01N 33/534; G01N 33/535
(52) U.S. Cl. ..................... 530/405; 435/188; 436/544; 436/545; 436/546; 436/815; 530/404; 546/69
(58) Field of Search ..................... 546/69; 436/544, 436/545, 546, 815; 435/188; 530/404, 405

(56) References Cited

U.S. PATENT DOCUMENTS

| 5,843,682 A | 12/1998 | Sigler et al. ............... 435/7.6 |
| 6,063,908 A | * 5/2000 | Salamone et al. | |
| 6,548,645 B1 | * 4/2003 | Sanchez et al. ............ 530/405 |

FOREIGN PATENT DOCUMENTS

| EP | 0816364 A1 | 1/1998 | ......... C07D/457/06 |
| EP | 0880029 A1 | 11/1998 | .......... G01N/33/94 |
| WO | 97/19100 | * 5/1997 | |
| WO | WO 99/42840 | 8/1999 | .......... G01N/33/94 |

OTHER PUBLICATIONS

Wendy A. Ratcliffe, et al., "Radioimmunoassay of Lysergic Acid Diethylamide (LSD) in Serum and Urine by Using Antisera of Different Specificities" Clinical Chemistry, vol. 23, No. 2, 1997 (pp. 169–174).

Ladislav Cvak, et al., "Side Reactions in Bromination of X–Ergocryptine" Galena, 747 70 Opava–Komdrov, Institute of Microbiology, Czechoslovak Academy of Sciences, 142 20 Praque 4, Collect. Czech. Chem. Commun. (vol. 57) (1992), (9 pgs).

Rodger L. Foltz, et al., "Metabolite Test Extends Time Period For Detecting LSD Use" Toxicology News, An AACC Educational Newsletter for Toxicology Laboratories, Dec. 1999, 4 pgs.

Zhuyin Li, et al., "New Synthesis and Characterization of (+)–Lysergic Acid Diethylamide (LSD) Derivatives and the Development of a Microparticle–Based Immunoassay for the Detection of LSD and Its Metabolites" Bioconjugate Chem. 1997, 8, 896–905.

Gregory K. Poch, et al., "Detection of Metabolites of Lysergic Acid Diethylamide (LSD) in Human Urine Specimens: 2–oxo–3–hydroxy–LSD, a Prevalent Metabolite of LSD" Journal of Chromatography B, 724 (1999) 22–23.

Scott A. Reuschel, et al., "Recent Advances in Chromatographic and Mass Spectrometric Methods for Determination of LSD and its Metabolites in Physiological Specimens" Journal of Chromatography B, 733 (1999) 145–159.

Scott A. Reuschel, et al., "Quantitative Determination of LSD and a Major Metabolite, 2–Oxo–3–Hydroxy–LSD, in Human Urine by Solid–Phase Extraction and Gas Chromatography–Tandem Mass Spectrometry" Journal of Analytical Toxicology, vol. 23, Sep. 1999 (pp. 306–312).

F. Troxler, et al., 87. "Oxydation von Lysergsauer–Derivaten in 2;3–Stellung" Volumen XLII, Fasciculus III (1959)–No 86–87 (pp. 793–802).

Abstract, Soft Tiaft 1998, Scientific Session 7, Friday Oct. 9, 1998, entitled Determination of 2–OXO–3–Hydroxy–LSD in Urine by GC/MS (7pgs).

* cited by examiner

*Primary Examiner*—Mary E. Ceperley
(74) *Attorney, Agent, or Firm*—Marilyn L. Amick; Roche Diagnostics Operations, Inc.

(57) ABSTRACT

The present invention provides hapten derivatives useful for the preparation of antigens, antibodies and reagents for use in immunoassays for the detection of LSD and 2-oxo-3-hydroxy LSD. In the present invention, the 2-oxy LSD nucleus is derivatized out of the indole nitrogen to form an aminoalkyl derivative. The resulting haptens can then be further modified at this functionalized position for linking to appropriate immunogenic or labeling groups to provide reagents for immunoassays having substantially equal specificity for both LSD and 2-oxo-3-hydroxy-LSD.

10 Claims, 7 Drawing Sheets

IMMUNOASSAY FOR LSD AND 2-OXO-3-HYDROXY-LSD

This application claims benefit of U.S. Provisional No. 60/196,030 filed Apr. 7, 2000.

BACKGROUND

The present invention relates to carboxyalkyl derivatives of 2-oxo-3-hydroxy-lysergic acid diethylamide (LSD) and to the use of these derivatives to prepare immunogens for stimulating antibody production. The antibodies so produced are useful in an immunoassay for determining LSD and 2-oxo-3-hydroxy-LSD. The invention also relates to a method for antibody screening.

The chemical structure of LSD is 9,10-didehydro-N,N-diethyl-6-methylergoline-8β-carboxamide and can be represented by the formula LSD is a highly potent hallucinogen, with the typical dosage range being 25 to 150 μg. The drug undergoes rapid and extensive metabolism, and only about 1% of the parent drug is actually excreted in human urine (Poch, G. K. et al., *J. Chromatogr. B* 724, 23–33, 1999). Possible metabolic transformations may be hydrolysis to lysergic acid, N-demethylation to N-desmethyl-LSD (nor-LSD) and oxidation to 2-oxo-LSD and 2-oxo-3-hydroxy-LSD. Isolysergic diethylamide (iso-LSD) is a byproduct of LSD synthesis and is often detected in the urine from an LSD user because of its presence as a contaminant in LSD sold on the street. The structure of iso-LSD is represented by the formula LSD is one of the most difficult drugs of abuse to detect in urine because of the very low concentrations of the parent drug excreted in the urine. 2-Oxo-3-hydroxy-LSD is a recently identified metabolite of LSD that has been found to be present in urine from LSD users at concentrations from 4 to 40 times higher than LSD and that can be detected for a longer time than LSD after ingestion of the drug (Reuschel, S. A., et al., *J. Anal. Toxicol.* 23, 306–312, 1999; Verstraete, A. G., Van de Velde, E. J., Annual Society of Forensic Toxicologists Meeting Scientific Session, Albuquerque, Ninn., Oct. 5–9, 1998).

In testing for other drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as β-galactosidase and peroxidase, fluorescent molecules such as fluorescein compounds, and radioactive compounds such as $^{125}I$ are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

Commercial immunoassay methods for LSD currently available employ monoclonal or polyclonal antibodies specific for LSD and having low cross-reactivity with 2-oxo-3-hydroxy-LSD. For example, the cross-reactivity of 2-oxo-3-hydroxy-LSD in the EMIT (Syva Company), CEDIA (Microgenics Corporation) and KIMS (Roche Diagnostics) immunoassays is 1.7, 1.8 and 11% respectively (Verstraete, A. G., ibid.). The present inventors are unaware of monoclonal antibodies specific for 2-oxo-3-hydroxy-LSD having been reported prior to their invention as described herein.

Haptens are partial or incomplete antigens. They are protein-free substances, mostly low molecular weight substances, which are not capable of stimulating antibody formation, but which do react with antibodies. The latter are formed by coupling the hapten to a high molecular weight carrier and injecting this coupled product into humans or animals. Examples of haptens include therapeutic drugs such as digoxin and theophylline, drugs of abuse such as morphine and LSD, antibiotics such as gentamycin and vancomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction such as by the attachment of a linking group for synthesizing a derivative conjugate.

A carrier, as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The term derivative refers to a chemical compound or molecule made from a parent compound or molecule by one or more chemical reactions.

Linking groups are used to activate, i.e., provide an available site on a drug derivative for synthesizing a hapten. The use of a linking group may or may not be advantageous or needed depending on the specific hapten and carrier pairs. The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur.

As used herein, a detector molecule, label or tracer is an identifying tag which, when attached to a carrier substance or molecule, can be used to detect an analyte. A label may be attached to its carrier substance directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}$I, A peptide is any compound formed by the linkage of two or more amino acids by amide (peptide) bonds, usually a polymer of α-amino acids in which the α-amino group of each amino acid residue (except the NH$_2$-terminal) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

As used herein, oxidized LSD means 2-oxo-3-hydroxy-LSD and 2-oxo-LSD.

DESCRIPTION OF THE INVENTION

The present invention provides novel LSD and iso-LSD hapten derivatives having the formula wherein $R_1$ and $R_2$ are independently selected from the group consisting of H and CON(CH$_2$CH$_3$)$_2$, provided that at least one of $R_1$ and $R_2$ is H; $R_3$ is H or OH; $R_4$ is a branched or straight chain linking group having 1–10 carbon atoms with 0–2 unsaturated bonds and 0–6 heteroatoms; and $R_5$ is selected from the group consisting of COR$_6$ and NHR$_7$, wherein $R_6$ is OH, L or LX and $R_7$ is H, L or LX, wherein L is a linking group and X is a detector or carrier molecule bound through L.

The invention also discloses novel antibodies derived from 2-oxo-3-hydroxy-LSD immunogens which exhibit high cross-reactivity with LSD and LSD conjugates. In another aspect of the invention, competitive immunoassay methods are provided for detection of 2-oxo-3-hydroxy-LSD and LSD in urine using the novel antibodies and an LSD conjugate.

The present invention is directed towards novel haptens and immunogens of oxidized LSD, antibodies derived from said immunogens, and immunoassay methods utilizing said antibodies. Oxidation of LSD to give 2-oxo-3-hydroxy-LSD is accomplished using modifications of procedures known in the art (Troxler, F., Hofmann, A., *Helv. Chim. Acta* 42, 793, 1959). In these procedures, an LSD salt is treated with two equivalents of a hypochlorite salt, preferably calcium hypochlorite, in a mixture of water and a water-miscible organic solvent, preferably acetonitrile. The reaction is carried out at a temperature of −10° C. to 30° C., preferably 0° C. to 5° C., for 0.5 to 2 hours. The reaction mixture is adjusted to basic pH and the product is extracted into an organic solvent. Purification is accomplished by column chromatography, preferably on neutral alumina. 2-Oxo-LSD can be obtained by reduction of the 2-oxo-3-hydroxy-LSD with zinc in acetic acid (Troxler, F., ibid.) or by controlled oxidation of LSD with N-bromosuccinimide (Siddik, Z. et al., *Biochemical Pharmacology* 28, 3081, 1979).

Novel hapten derivatives of oxidized LSD alkylated at the indole nitrogen, i.e., the N-1 position, are prepared under mild conditions using a bifunctional haloalkyl linker which contains a protected functionality at the end opposite the halogen atom. Examples of preferred protected functionalities are protected amines and carboxylic acids. Some preferred examples of bifunctional haloalkyl linkers are ethyl iodobutyrate and N-iodopropyl-phthalimide. Other examples of bifunctional haloalkyl linkers will be readily apparent to those skilled in the art. Alkylation is readily accomplished by substitution of the halogen atom by the pyrollidone nitrogen of oxidized LSD in the presence of a base. A surprisingly mild reaction condition has been found for this alkylation in which an alkali metal carbonate is used as base in the presence of a crown ether. A preferred alkali metal carbonate/crown ether combination is potassium carbonate and 18-crown-6. It has been found that the reaction is most favored when the amount of crown ether added is equimolar or greater than the amount of potassium carbonate. In other words, more than catalytic amounts are required. The reaction is performed in a dipolar aprotic solvent, preferably dimethylformamide (DMF) at a temperature range of 20–100° C., preferably 50–70° C., for 1–24 hours. The alkylated product is then isolated and the protecting group is removed from the linking group under conditions that do not give rise to side-reactions on the oxidized-LSD. Examples of such conditions are saponification with lithium hydroxide to remove an alkyl ester and generate free carboxylic acid or methylamine treatment to remove a phthalimido protecting group and generate free amine.

The deprotected N-1-alkylated oxidized LSD with a free carboxyl group or an amine terminus may be used directly for preparation of conjugates. For example, oxidized LSD with carboxyl linking groups may be conjugated to amines on carriers, labels or tracers using condensation reagents well known in the art for formation of amide bonds. Similarly amine groups may be conjugated to carboxyl groups on carriers, labels or tracers. However, it is particularly preferred to conjugate the N-1-alkylated oxidized LSD with free carboxyl or amine terminus to a second linking group. These second linking groups may be a variety of heterobifunctional or homobifunctional linkers which are well-known in the art. For instance, in the case of a first linking group which terminates in carboxyl group, examples of second linking groups are maleimidoalkylamines as described in PCT publication WO90/15798 and amino acids. These amine containing second linking groups are typically reacted with carboxyl group on the first linker using any one of a large number of condensation reagents known in the art for formation of amide bonds. In the case where the first linker terminates in an amine, examples of preferred second linkers are terephthalic acid di-N-hydroxysuccinimide ester, 1,1'-biphenyl-4,4'-di-N-hydroxysuccinimide, 4-isothiocyanato-benzoylchloride, 3-maleimidopropionic acid N-hydroxysuccinimide ester (MPS), S-acetylthiopropionic acid-N-hydroxysuccinimide ester (SATP). The N-hydroxysuccinimide ester second linkers are typically reacted directly with the amine containing first linker under mild conditions.

In the case of the di-N-hydroxysuccinimide ester, the reaction is carried out under conditions which favor the formation of mono-substituted product rather than di-substituted product. For example, dropwise addition of the oxidized LSD N-1-linker amine to di-N-hydroxysuccinimide ester will favor mono-substitution. After attachment of the second linker to the oxidized LSD, a new terminal functional group on the second linker is present. In the case of the di-N-hydroxysuccinimide esters second linkers, the new terminal functional group is simply the unreacted N-hydroxysuccinimide ester obtained from mono-substitution. This latter group is ready for conjugation to amine groups on carriers, labels and tracers by direct condensation to give amide bonds. Similarly, when the terminal linker group is an isothiocyanate, direct conjugation to amine groups on carriers, labels and tracers may be performed at this stage to give thiourea bonds.

In the case where the new terminal functional group is a maleimide, as with MPS, conjugation is accomplished by addition to thiol groups on carriers, labels and tracers to give thioether bonds. The thiol groups may be inherent to the carriers, labels and tracers or may be introduced by thiolating agents such as SATP.

In the case where the new functional group is a thiol or protected thiol as with SATP, the thiol is conjugated directly or subsequent to deprotection with a maleimide-modified immunogen or label. Many more variations of linker chemistries will be obvious to those skilled in the art, and these are only presented for the sake of illustration. For a comprehensive treatment of homobifunctional and heterobifunctional linking groups and the reaction conditions for their attachment to amines and carboxylic acids, the reader is referred to *Bioconjugate Techniques*, G. Hermanson, Academic Press, (1995).

According to a preferred embodiment, in preparing the immunogens of the invention, a carrier poly(amino acid) or other substance having immunogenic properties is coupled to the activated hapten. Although bovine thyroglobulin is an especially preferred antigenic poly(amino acid) or carrier protein, it should be understood that any protein carrier may be employed, including such things as albumins, serum proteins, e.g., globulins, ocular lens proteins, lipoproteins and the like. Illustrative protein carriers include keyhole limpet hemocyanin (KLH), bovine serum albumin, egg ovalbumin, bovine gammaglobulin, etc. Alternatively, synthetic poly(amino acids) may be employed, as may other synthetic or natural polymeric materials bearing reactive functional groups. In particular, carbohydrates, yeasts, or polysaccharides may be conjugated to the hapten to produce an immunogen.

The hapten derivatives can also be coupled to a variety of tracer, detection or labeling molecules by methods well known in the art to provide a variety of reagents useful in different immunoassay formats. For detection, there can be attached detector molecules such as fluorophores, for example fluorescein to produce tracers, or radiolabeled or chemiluminescent groups. The hapten can be bound to microparticles including colored latex for use in spectrophotometric or direct optical detection formats such as latex agglutination or chromatographic strip tests. The attached group may also be an indirect detection molecule such as an energy transfer partner, enzyme or other group that is detected by further chemical reaction.

In the present invention, the 2-oxo-3-hydroxy-LSD hapten derivatives are activated and coupled to proteins, for example carrier proteins such as BSA or BTG, to form immunogens. Additionally, these carrier groups are used to form reagents for immunoassay, i.e., tethers for the attachment of the haptens to solid matrices, or labeling groups such as microparticles, radioactive labels etc., forming label-conjugates. The label-conjugates are used as reagents in immunoassays or in ELISA microtiter plate assays for competing with the drug for binding to antibodies. The label-conjugate can be used, for example, in certain assay formats to coat microtiter assay plates.

In order to generate antibodies, the immunogen is conveniently prepared for injection into a host animal by rehydrating lyophilized immunogen to form a solution or suspension of the immunogen. The immunogen solution is then combined with an adjuvant such as Freund's. The immunogen may be administered in a variety of sites, at several doses, one or more times, over many weeks.

Preparation of polyclonal antibodies using the immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, immunized as described above, and myeloma cells using a polyethylene glycol method such as the technique described in *Methods in Enzymology* 73 (Part B), pp. 3–46, 1981.

EXAMPLES

Figure 1:
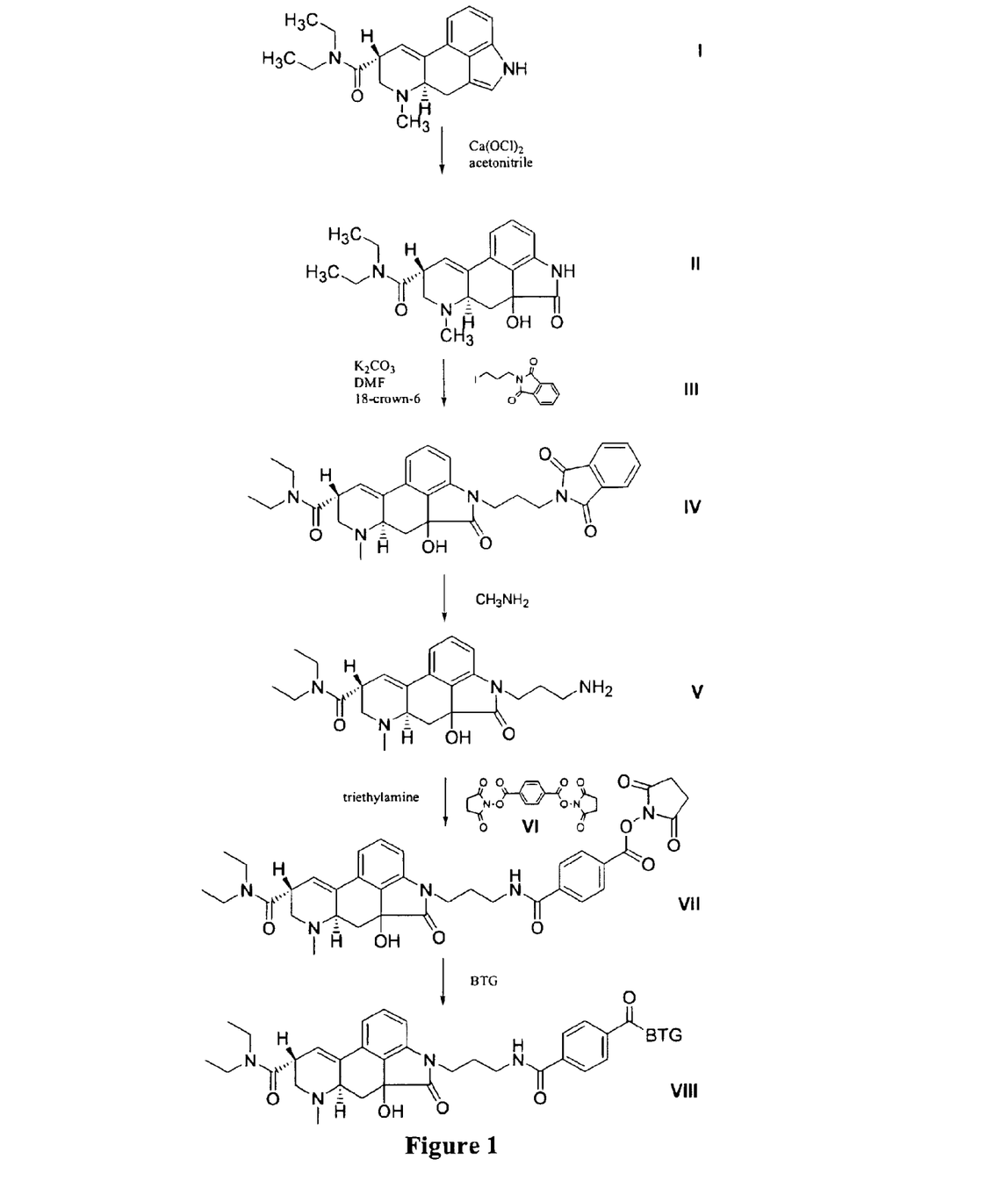
FIG. 1 shows the synthesis of an activated 2-oxo-3-hydroxy-LSD hapten and a 2-oxo-3-hydroxy-LSD immunogen of the present invention.
Figure 2:
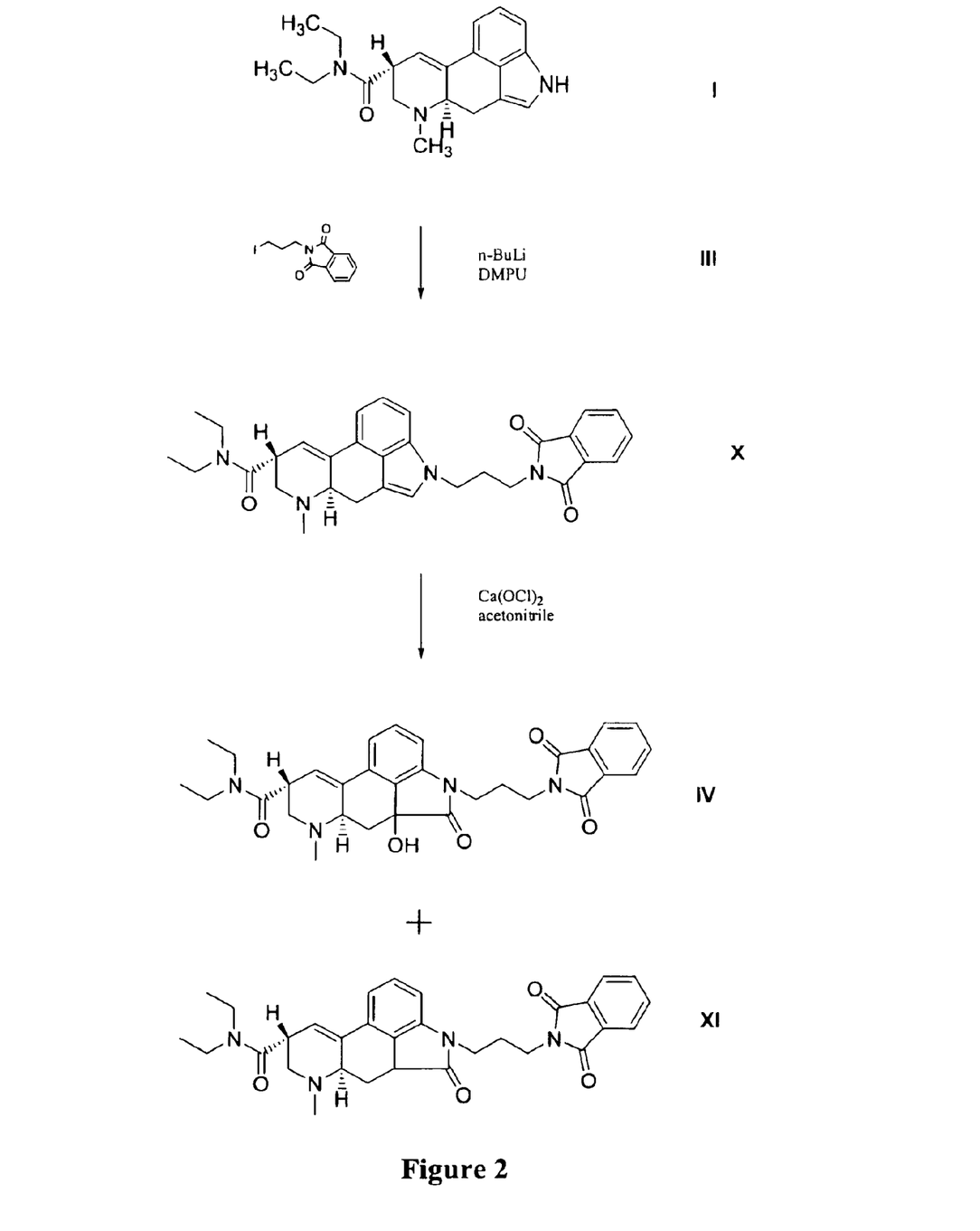
FIG. 2 shows an alternate synthesis of a 2-oxo-3-hydroxy-LSD derivative and a 2-oxo-LSD derivative.
Figure 3:
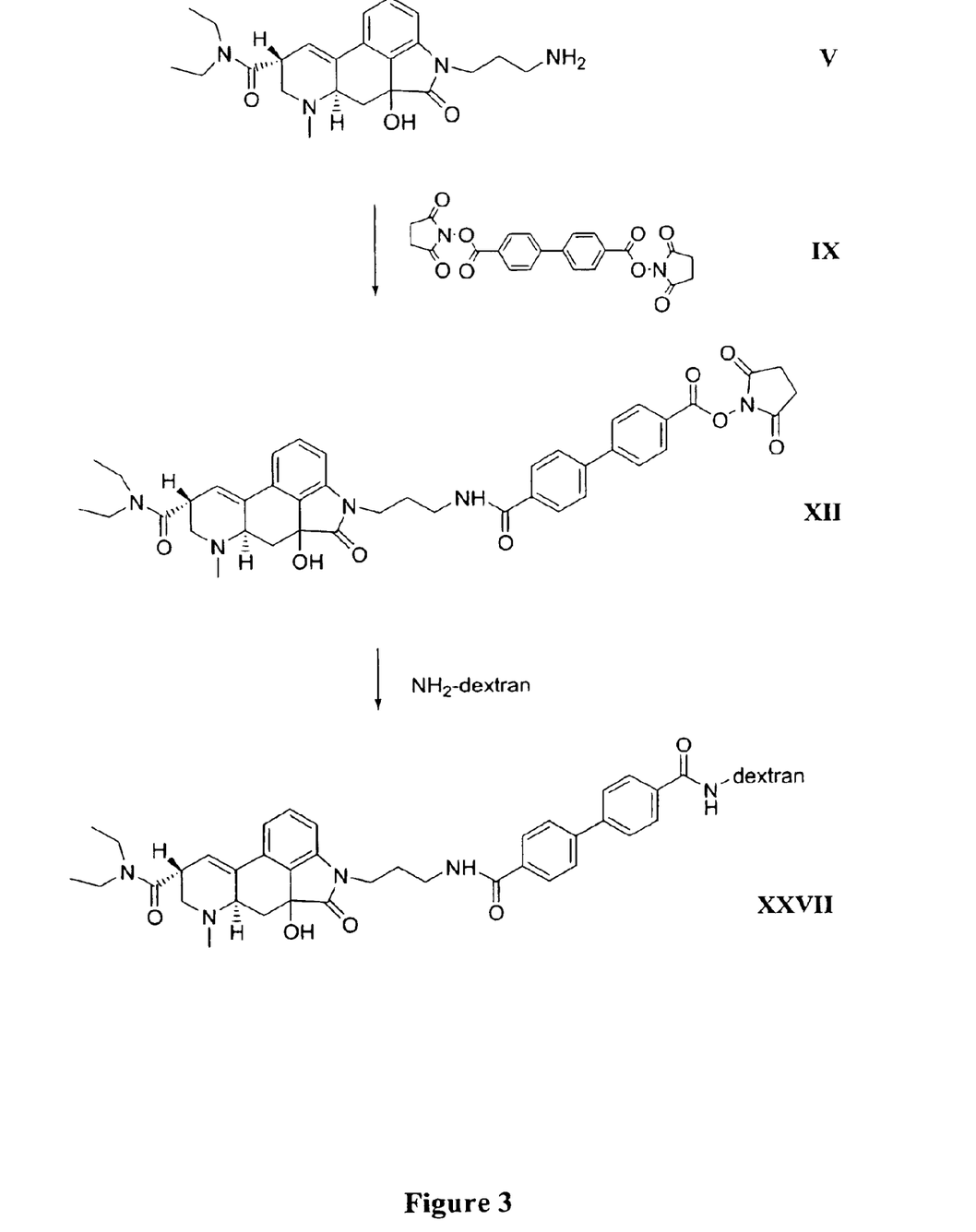
FIG. 3 shows the synthesis of a preferred conjugate of the present invention.
Figure 4:
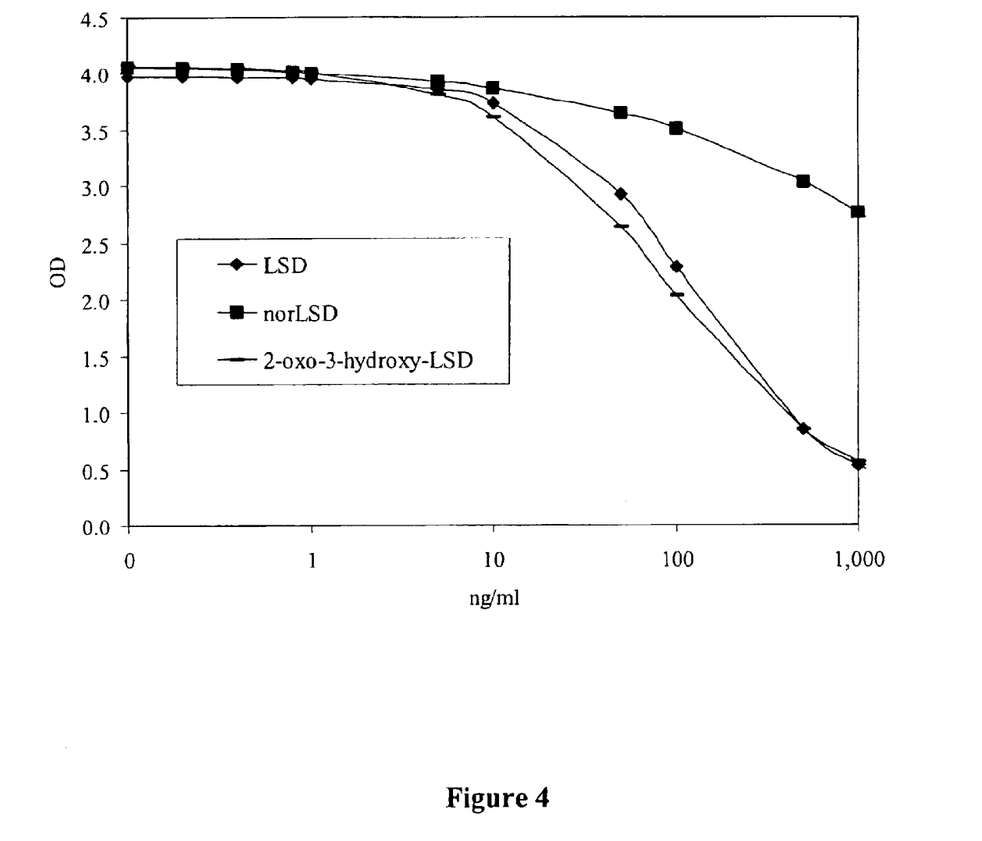
FIG. 4 is a data plot showing the reactivity of clone 1.1 with LSD, nor-LSD and 2-oxo-3-hydroxy-LSD.
Figure 5:
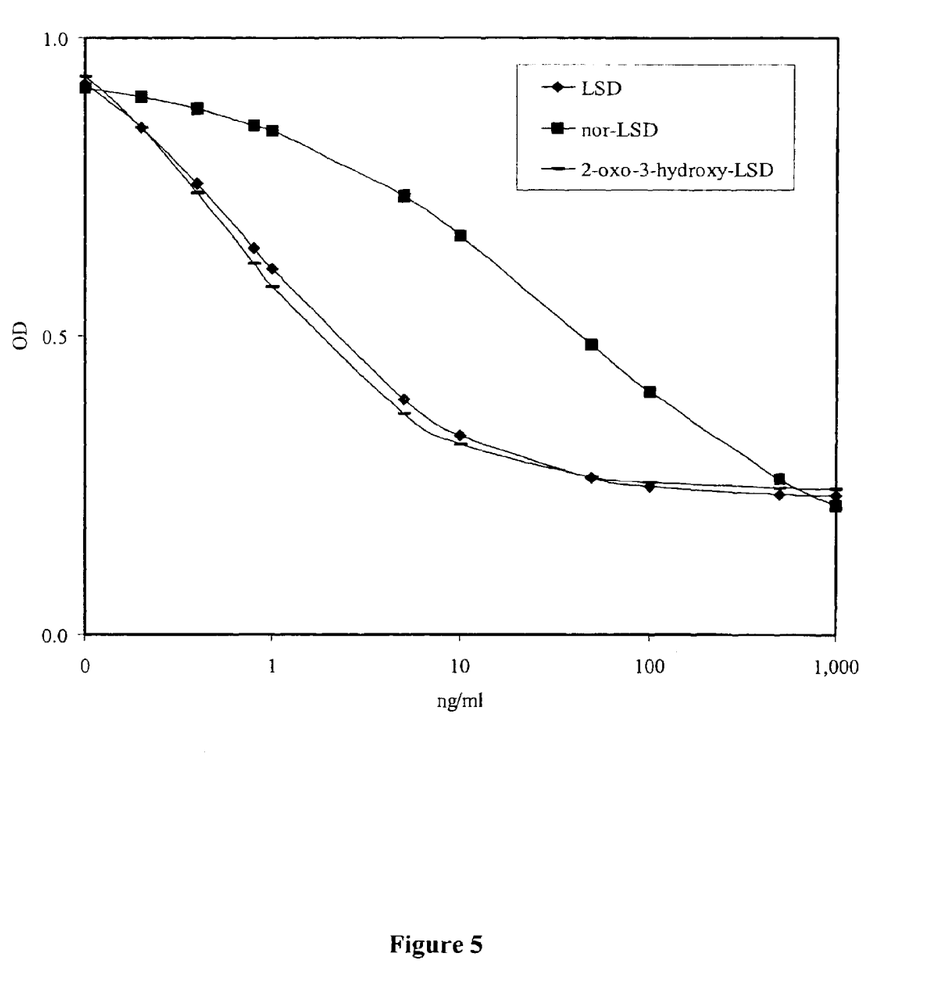
FIG. 5 is a data plot showing the reactivity of clone 2.1 with LSD, nor-LSD and 2-oxo-3-hydroxy-LSD.
Figure 6:
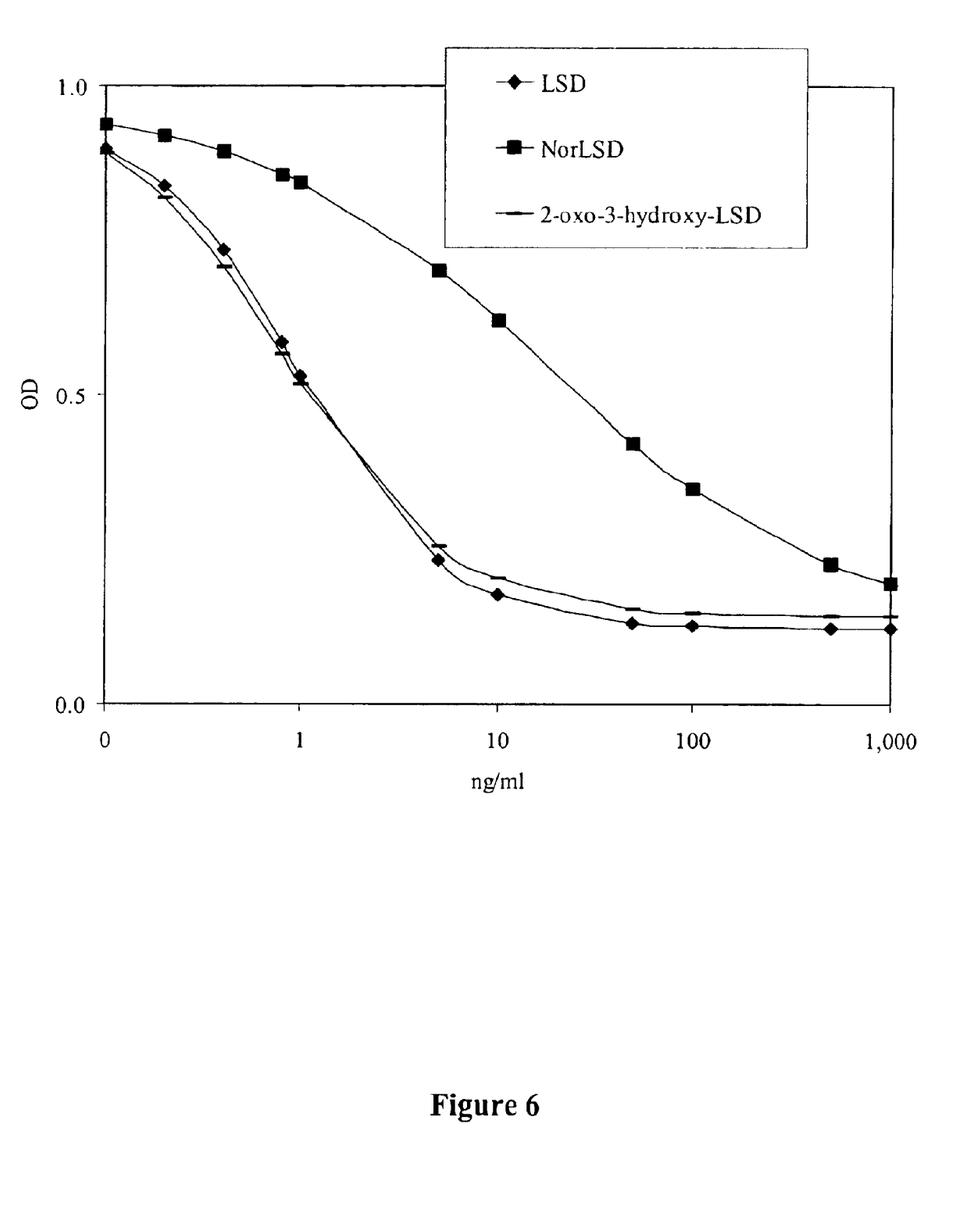
FIG. 6 is a data plot showing the reactivity of clone 20.2 with LSD, nor-LSD and 2-oxo-3-hydroxy-LSD.

Roman numerals used in the following examples refer to the corresponding chemical structure diagrammed in FIGS. 1, 2 and 3.

Example 1

Synthesis of D-lysergic Acid Diethylamide (I)

A mixture of 10.0 g (0.037 mol) of d-lysergic acid in 500 ml of dry dimethyl formamide (DMF), under argon, was treated with 9.0 g of carbonyl diimidazole and stirred at room temperature for 1 hour The reaction was then treated with 38 ml of diethylamine and stirred at room temperature overnight. The reaction was concentrated under reduced pressure. The residue was taken up in 500 ml of methylene chloride and washed with 500 ml of water. Insoluble material was removed by filtration and the layers were separated. The organic portion was washed with 250 ml of saturated brine solution, dried over anhydrous sodium sulfate and concentrated under reduced pressure. The residue was chromatographed on 800 g of silica gel using 3% methanol in methylene chloride to yield 9.0 g (75%) of d-lysergic acid diethylamide (LSD) as a light brown amorphous solid after evaporation of the solvents.

Example 2

Synthesis of 2-oxo-3-hydroxy-d-lysergic Acid Diethylamide (II)

A solution of 500 mg (1.55 mmol) of LSD in 5 ml of acetonitrile was cooled with an ice bath and treated with a solution of 354 mg of 1-tartaric acid in 25 ml of water. A solution of calcium hypochlorite was prepared by treating 442 mg of calcium hypochlorite with 25 ml of water and stirring vigorously. The cloudy solution was filtered through a 0.45 µm Millex-HV filter, then cooled with an ice bath. This was added to the LSD-tartrate solution and the reaction stirred at 0° C.–5° C. for 45 minutes. The reaction was diluted with 200 ml of saturated sodium bicarbonate solution and extracted with 6×250 ml of chloroform The chloroform extracts were combined and concentrated under reduced pressure. The residue was chromatographed on 500 g of neutral alumina using one liter of 5% methanol in methylene chloride to remove higher front running impurities, then 10% methanol in methylene chloride to elute the product to yield 160 mg (29%) of brown solid after evaporation of solvents.

Example 3

Synthesis of N-(3-iodopropyl)phthalimide (III)

A solution of 50.0 g (0.187 mol) of N-(3-bromopropyl)phthalimide in 1.2 L of acetone was treated with 208.5 g of potassium iodide and stirred at room temperature for 4 days. The reaction was filtered and the filtrate was diluted with 4 L of ether. This was then filtered through CELITE. The filtrate was concentrated under reduced pressure to a yellow solid. This was recrystallized from hexane to yield 46.5 g (79%) of off-white solid.

Example 4

Synthesis of N-1-(3-phthalimidopropyl)-2-oxo-3-hydroxy-LSD (IV)

A solution of 600 mg (1.69 mmol) of 2-oxo-3-hydroxy-LSD in 30 ml of dry DMF was treated with 600 mg (4.34 mmol) of anhydrous potassium carbonate, 600 mg (1.9 mmol) of N-(3-iodopropyl)phthalimide and 1.9 g (7.19 mmol) of 18-crown-6. The reaction was stirred at 60° C. for 45 minutes. The reaction was concentrated under reduced pressure, dissolved in methylene chloride, washed with 8×200 ml of water, dried over anhydrous sodium sulfate and concentrated at reduced pressure. The residue was chromatographed on 100 g of silica gel using 5% methanol in methylene chloride to remove higher front running impurities, then 10% methanol in methylene chloride to elute the product and yield 467 mg (51%) of yellow solid after evaporation of solvents.

Example 5

Synthesis of N-1-(3-aminopropyl)-2-oxo-3-hydroxy-LSD (V)

367 mg (0.68 mmol) of 1-(3-(phthalimidopropyl)-2-oxo-3-hydroxy-LSD, under argon, was treated with 30 ml of 2M methylamine in methanol and stirred at room temperature for 3 hrs. The reaction was concentrated at reduced pressure. The residue was chromatographed on 30 g of silica gel using 30% methanol in methylene chloride to remove higher front running impurities, then using 2% triethylamine/30% methanol/68% methylene chloride to elute the product to yield 138 mg (49%) of yellow amorphous solid after evaporation of solvents.

Example 6

Synthesis of Terephthalic Acid di-N-hydroxysuccinimide Ester (VI)

To 15 g (73.8 mmol) of terephthaloyl chloride was added 300 mL of methylene chloride and the solution was cooled to 0° C. for about 10 minutes. To this solution was added 30 g of N-hydroxysuccinimide followed by 30 ml of triethylamine dropwise. The mixture was allowed to stir at 0° C. for 1 hr and at room temperature for 48 hr. The reaction mixture was filtered and the residue was washed with 200 ml of methylene chloride. The solid was resuspended in 300 ml of methylene chloride and allowed to stir for 10 minutes at room temperature. The solid was filtered and dried under vacuum to give 24.1 g (67 mmol, 90%) of product.

Example 7

Synthesis of N-1-(3-[4-(succinimido-oxycarbonyl)-phenyl-1-carbonylamino]-propyl)-2-oxo-3-hydroxy-LSD (VII)

A solution of 41 mg (0.114 mmol) of terephthalic acid di-N-hydroxysuccinimide ester in 20 ml of dry tetrahydrofuran, under argon, was treated with a solution of 47 mg (0.114 mmol) of 1-(3-aminopropyl)-2-oxo-3-hydroxy-LSD in 10 ml of dry tetrahydrofuran and 0.2 ml of triethylamine added dropwise over 30 minutes. The reaction was stirred at room temperature overnight. The reaction was concentrated under reduced pressure. The residue was chromatographed on 5 g of silica gel using ethyl acetate to remove higher front running impurities, then distilled tetrahydrofuran to elute the product and yield 40 mg (53%) of tan solid after evaporation of solvents.

Example 8

Synthesis of 2-oxo-3-hydroxy-LSD Immunogen (VIII)

A solution of 270 mg of bovine thyroglobulin (BTG) in 4.5 ml of 50 mM potassium phosphate (pH 7.5) was cooled in ice-bath. To the solution 15 ml of dimethylsulfoxide (DMSO) was added dropwise and the reaction temperature was maintained below room temperature. To the protein solution was added a solution of 40 mg (0.062 mmol) of 2-oxo-3-hydroxy-LSD monophenyl NHS ester derivative (VII) in 1 ml of DMF dropwise. The mixture was allowed to stir at room temperature 18 h. The resulting conjugate was placed in a dialysis tube (50,000 mw cut-off) and was dialyzed in 2 L of 70% DMSO in 50 mM potassium phosphate (pH 7.5) [3 changes, at least 3 h each], 2 L of 50% DMSO in 50 mM potassium phosphate (at least 3 h), 2 L of 30% DMSO in 50 mM potassium phosphate (at least 3 h), 10% DMSO in 50 mM potassium phosphate (at least 3 h) at room temperature followed by 6 changes with 50 mM potassium phosphate (pH 7.5) at 4° C. (2 L each for at least 6 h each). The protein concentration was determined to be 6.84 mg/ml using Biorad Coomassie blue protein assay.

Bradford, M., Anal. Biochem., 72, 248 (1976). A total volume of 35 ml of 2-oxo-3-hydroxy-LSD BTG immunogen was prepared. The extent of available lysine modification was determined to be 60% by the TNBS method. Habeeb AFSA, Anal. Biochem. 14, 328–34 (1988).

Example 9

Synthesis of 1,1'-biphenyl-4,4'-di-N-hydroxysuccinimide Ester (IX)

A mixture of 24.0 g (0.1 mol) of 1,1'-biphenyl-4,4'-dicarboxylic acid in 480 ml of dry tetrahydrofuran was treated with 60 ml of oxalyl chloride followed by 0.24 ml of dry DMF, stirred at room temperature for 10 minutes then heated to reflux for 90 minutes. The reaction was concentrated under reduced pressure to a yellow solid. This was taken up in 200 ml of dry tetrahydrofuran and concentrated under reduced pressure. This step was repeated 2 more times to drive off residual oxalyl chloride. The product was triturated with ether and collected by suction filtration to yield 25.6 g (93%) of 1,1'-biphenyl-4,4'-dicarbonyl chloride as a yellow solid.

A solution of 11.5 g (0.04 mol) of 1,1'-biphenyl-4,4'-dicarbonyl chloride in 500 ml of dry methylene chloride was treated with 25.0 g (0.22 mol) of N-hydroxysuccinimide followed by 25 ml of triethylamine and stirred at room temperature overnight. The resulting solid was collected by suction filtration to yield 11.58 g of white solid. The filtrate was concentrated under reduced pressure to a brown solid. This was triturated with methylene chloride with stirring for 1 hour, following which 5.56 g of white solid was collected. This gave a combined yield of 17.14 g (95%).

Example 10

Synthesis of 4-isothiocyanatobenzoyl Chloride

A mixture of 500 mg (2.79 mmol) of 4-carboxyphenylisothiocyanate and 5 ml of thionyl chloride was refluxed for 6 hours. The reaction mixture was concentrated at reduced pressure and the resulting tan solid was pumped at high vacuum overnight. The solid was triturated with a small amount of hexane and collected by suction filtration to yield 516 mg (93%) of product as an off-white solid.

Example 11

Synthesis of N-1-(3-[4-isothiocyanatophenyl-1-carbonylamino]-propyl)-2-oxo-3-hydroxy-LSD A solution of 1.0 mmol of 4-isothiocyanatobenzoylchloride in 15 ml of dry tetrahydrofuran, under argon, is cooled to 0° C. and treated with a solution of 1.0 mmol of 1-(3-aminopropyl)-2-oxo-3-hydroxy-LSD in 10 ml of dry tetrahydrofuran. The reaction is treated with 1.0 mmol of triethylamine, stirred at 0° C. for 30 minutes, then at room temperature overnight. The reaction is concentrated under reduced pressure. The residue dissolved in methylene chloride, washed with water, dried over anhydrous sodium sulfate and concentrated under reduced pressure. The residue is chromatographed on silica gel using 10% methanol in methylene chloride to yield the desired product.

Example 12

Synthesis of N-1-(3-[4'-succinimido-oxycarbonyl-1,1'-biphenyl-4-carbonylamino]propyl)-2-oxo-3-hydroxy-LSD (XII)

A solution of 146 mg (0.33 mmol) of 1,1'-biphenyl-4,4'-di-N-hydroxysuccinimide ester (XI) in 70 ml of dry tetrahydrofuran, under argon was treated with a solution of 138 mg (0.33 mmol) of 1-(3-aminopropyl)-2-oxo-3-hydroxy-LSD in 25 ml of dry tetrahydrofuran and 0.55 ml of triethylamine added dropwise over 30 minutes. The reaction was stirred at room temperature overnight. The reaction was concentrated under reduced pressure. The residue was chromatographed on 20 g of silica gel using ethyl acetate to remove higher front running impurities, then distilled tetrahydrofuran to elute the product to yield 90 mg (37%) of tan solid after evaporation of solvents.

Example 13

Synthesis of 1-(3-phthalimidopropyl)-2-oxo-LSD

A solution of 1.0 mmol of 2-oxo-LSD in 20 ml of dry DMF is treated with 2.6 mmol of anhydrous potassium carbonate, 1.2 mmol of N-(3-iodopropyl)phthalimide and 4.0 mmol of 18-crown-6. The reaction is stirred at 60° C. for 45 minutes. The reaction is concentrated under reduced pressure, dissolved in methylene chloride, washed with 10×100 ml of water, dried over anhydrous sodium sulfate and concentrated at reduced pressure. The residue is chromatographed on silica gel using 5% methanol in methylene chloride to remove higher front running impurities, then 10% methanol in methylene chloride to yield the desired product.

Example 14

Synthesis of 1-(3-aminopropyl)-2-oxo-LSD 1.0 mmol of 1-(3-phthlalimidopropyl)-2-oxo-LSD, under argon, is treated with 50 ml of 2M methylamine in methanol and stirred at room temperature for 3 hrs. The reaction is concentrated at reduced pressure. The residue is chromatographed on 50 g of silica gel using 30% methanol in methylene chloride to remove higher front running impurities, then using 2% triethylamine/30% methanol/68% methylene chloride to yield the desired product after evaporation of solvents.

Example 15

Synthesis of N-1(3-[4-(succinimido-oxycarbonyl)-phenyl-1-carbonylamino]-propyl)-2-oxo-LSD A solution of 1.0 mmol of terephthalic acid di-N-hydroxysuccinimide ester in 200 ml of dry tetrahydrofuran, under argon, is treated with a solution of 1.0 mmol of 1-(3-aminopropyl)-2-oxo-LSD in 75 ml of dry tetrahydrofuran and 2.0 ml of triethylamine added dropwise over 30 minutes. The reaction is stirred at room temperature overnight. The reaction is concentrated under reduced pressure. The residue is chromatographed on silica gel using ethyl acetate to remove higher front running impurities, then distilled tetrahydrofuran to yield the desired product after evaporation of solvents.

Example 16

Synthesis of N-1-(3-[4'-succinimido-oxycarbonyl-1,1'-biphenyl-4-carbonylamino]propyl)-2-oxo-LSD A solution of 1.0 mmol of 1,1'-biphenyl-4,4'-di-N-hydroxysuccinimide ester in 200 ml of dry tetrahydrofuran, under argon, is treated with a solution of 1.0 mmol of 1-(3-aminopropyl)-2-oxo-LSD in 75 ml of dry tetrahydrofuran and 2.0 ml of triethylamine added dropwise over 30 minutes. The reaction is stirred at room temperature overnight. The reaction is concentrated under reduced pressure. The residue is chromatographed on silica gel using ethyl acetate to remove higher front running impurities, then distilled tetrahydrofuran to yield the desired product after evaporation of solvents.

Example 17

Synthesis of N-1-(3-[4-isothiocyanatophenyl-1-carbonylamino]-propyl)-2-oxo-LSD

A solution of 1.0 mmol of 4-isothiocyanatobenzoylchloride in 15 ml of dry tetrahydrofuran, under argon, is cooled to 0° C. and treated with a solution of 1.0 mmol of 1-(3-aminopropyl)-2-oxo-N,N-diethyl-d-lysergamide in 10 ml of dry tetrahydrofuran. The reaction is treated with 1.0 mmol of triethylamine, stirred at 0° C. for 30 minutes, then at room temperature overnight. The reaction is concentrated under reduced pressure. The residue is dissolved in methylene chloride, washed with water, dried over anhydrous sodium sulfate and concentrated under reduced pressure. The residue is chromatographed on silica gel using 10% methanol in methylene chloride to yield the desired product after evaporation of solvents.

Example 18

Synthesis of N-1-(3-carboxypropyl)-2-oxo-LSD

A solution of 1.0 mmol of 2-oxo-LSD in 20 ml of dry DMF is treated with 2.6 mmol of anhydrous potassium carbonate, 1.2 mmol of ethyl iodobutyrate and 4.0 mmol of 18-crown-6. The reaction is stirred at 60° C. for 45 minutes. The reaction is concentrated under reduced pressure, dissolved in methylene chloride, washed with 10×100 ml of water, dried over anhydrous sodium sulfate and concentrated at reduced pressure. The residue is chromatographed on silica gel using methanol in methylene chloride to yield the ethyl ester of product. A solution of 1.0 mmol of the ethyl ester in 10 ml of a 1:1 mixture of THF and methanol is treated with a solution of 10 mmol of lithium hydroxide monohydrate and stirred at room temperature overnight. The reaction mixture is concentrated at reduced pressure. The aqueous residue is adjusted to pH 6 and extracted with methylene chloride, dried over sodium sulfate and concentrated at reduced pressure. The residue is purified by silica gel column chromatography using a mixture of 9:1 methylene chloride/methanol as eluent.

Example 19

Synthesis of N-1-(3-carboxypropyl)-2-oxo-3-hydroxy-LSD

A solution of 1.0 mmol of 2-oxo-3-hydroxy-LSD in 20 ml of dry DMF is treated with 2.6 mmol of anhydrous potassium carbonate, 1.2 mmol of ethyl iodobutyrate and 4.0 mmol of 18-crown-6. The reaction is stirred at 60° C. for 45 minutes. The reaction is concentrated under reduced pressure, dissolved in methylene chloride, washed with 10×100 ml of water, dried over anhydrous sodium sulfate and concentrated at reduced pressure. The residue is chromatographed on silica gel using methanol in methylene chloride to yield the ethyl ester of product. A solution of 1.0 mmol of the ethyl ester in 10 ml of a 1:1 mixture of THF and methanol is treated with a solution of 10 mmol of lithium hydroxide monohydrate and stirred at room temperature overnight. The reaction mixture is concentrated at reduced pressure. The aqueous residue is adjusted to pH 6 and extracted with methylene chloride, dried over sodium sulfate and concentrated at reduced pressure. The residue is purified by silica gel column chromatography using a mixture of 9:1 methylene chloride/methanol as eluent.

Example 20

Synthesis of N-1-(3-phthalimidopropyl)-LSD (X)

A solution of 8.0 g (24.7 mmol) of LSD in 160 ml of dry tetrahydrofuran was cooled to −78° C. To the reaction mixture was added 11 ml of 2.5 M n-butyl lithium followed by 80 ml of N,N'-dimethylpropylene urea (DMPU) and the reaction was allowed to stir for 20 minutes. A solution of 12 g (38 mmol) of iodopropyl phthalimide in 25 ml of DMPU was added and the mixture was allowed to stir at −78° C. for 90 minutes. The reaction was allowed to warm up to room temperature with stirring for 2 hours. The tetrahydrofuran was removed in vacuo and the oily residue was diluted with 500 ml of ethyl acetate. This was washed with 5×250 ml of water, dried over sodium sulfate and concentrated to give a dark oil. This was purified by silica gel column using 3% methanol in dichloromethane as eluent to give 6.65 g (13 mmol, 53%) of product.

Example 21

Synthesis of N-1-(3-phthalimidopropyl)-2-oxo-3-hydroxy-LSD (IV) and N-1-(3-phthalimidopropyl)-2-oxo-LSD (XI)

To a solution of 25 mg (0.048 mmol) of N-1-(3-phthalimidopropyl)-LSD was added 1 ml of HPLC grade acetonitrile. The reaction mixture was cooled to 4° C. A solution of L-tartaric acid (12 mg, 0.079 mmol) in 1 ml of water was cooled to 4° C. and added to the LSD-N-aminopropylphthalimide solution.

A suspension of 11 mg (0.076 mmol) of calcium hypochlorite in 1 ml of water was filtered through Millex HV filter (4.5 µm), cooled to 4° C. and added to the cooled and magnetically stirred LSD N-aminopropylphthalimide tartrate solution. The reaction mixture was allowed to stir at 4° C. for 10 minutes and 15 ml of saturated sodium bicarbonate solution was added. The reaction mixture was warmed up to room temperature and was extracted with 5×30 ml of chloroform. The combined organic layer was dried (anhydrous sodium sulfate) and concentrated. The residue was purified by preparative silica gel chromatography using 10% methanol in chloroform to give 5 mg (0.009 mmol, 20%) of N-1-(3-phthalimidopropyl)-2-oxo-LSD and 8 mg (0.014 mmol, 30%) of N-1-(3-phthalimidopropyl)-2-oxo-3-hydroxy-LSD.

Example 22

Synthesis of 2-oxo-3-hydroxy-LSD-BSA ELISA Screening Conjugate

A solution of 400 mg of bovine serum albumin (BSA) in 6 ml of 50 mM potassium phosphate (pH 7.5) was cooled in ice-bath. To the solution was added 6 ml of DMSO dropwise and the reaction temperature was maintained below room temperature. To the protein solution was added a solution of 10 mg (0.015 mmol) of 2-oxo-3-hydroxy-LSD monophenyl NHS ester derivative (VII) in 1 ml of anhydrous DMF dropwise. The reaction mixture was allowed to stir at room temperature 18 h. The resulting conjugate was placed in a dialysis tube (10,000 mw cut-off) and was dialyzed sequentially in 2 L of 60% DMSO in 50 mM potassium phosphate [3 changes, at least 3 h each], 2 L of 50% DMSO in 50 mM potassium phosphate (at least 3 h), 2 L of 30% DMSO in 50 mM potassium phosphate (at least 3 h), 10% DMSO in 50 mM potassium phosphate (at least 3 h) at room temperature followed by 6 changes with 50 mM potassium phosphate (pH 7.5) at 4° C. (2 L each for at least 6 h each). A total of 30 ml of 2-oxo-3-hydroxy-LSD BSA conjugate was obtained. The protein concentration was determined to be 8.8 mg/ml using Biorad Coomassie blue protein assay.

Example 23

Synthesis of LSD-BSA ELISA Screening Conjugate

N-1-[(4-isothiocyanatophenyl-carbonyl)aminobutyl]-LSD was synthesized by the procedure given in Example 7 of EP 0 816 364 A1. A solution of 1.0 g of BSA in 16 ml of 50 mM potassium phosphate (KPI) pH 7.5 buffer was cooled with an ice bath and treated with a solution of N-1-[(4-isothiocyanatophenyl)carbonyl)aminobutyl]-LSD in 1.5 ml of DMF added slowly, then stirred at room temperature overnight. The reaction mixture was placed in dialysis tubing, 15,000 MW cutoff and dialyzed in 2 liters of 10% DMF-90% 50 mM KPI, pH 7.5 at room temperature for 3 hours, followed by 2 L of 100% 50 mM KPI pH 7.5 at room temperature for 4 hours, and finally 2 L of 100% 50 mM KPI pH 7.5 at 4° C., 5 changes, at least 6 hours each. Final volume of conjugate was 24 ml. Coomassie blue protein assay gave a protein concentration of 38.2 mg/ml. Protein recovery was 916.8 mg (92%).

Example 24

Hybridoma Development

Mice were immunized with 2-oxo-3-hydroxy-LSD-BTG conjugate three times. The first immunization was of 100 micrograms emulsified in Complete Freund's Adjuvant, by both the hind foot pad and intraperitoneal routes. Four weeks later a secondary immunization of the same amount (in incomplete Freund's adjuvant) and routes was administered. Fourteen days later the mice were bled retro-orbitally to obtain blood samples for analysis. ELISA analysis on the clarified serum revealed that three of the four mice showed antibody titers of greater than $4 \times 10^5$, as defined as the 50% inflection point of the serum dilution series. Fourteen days after the bleeds were taken, the mice were again immunized as above.

When the fusion was planned, the mouse showing the highest antibody serum titer was boosted by the injection of 50 μg of immunogen in phosphate buffered saline via both routes. Four days later the animal was sacrificed and the spleen and inguinal and popliteal lymph nodes harvested. These cells were fused to the FO myeloma line via standard techniques. (St Groth, D. E. et al., *J. Immunol. Meth.* 35, 1–21, 1980). The fused cells were distributed into sterile 96 well plates at a density of $4 \times 10^4$ lymphocytes per well in standard hybridoma selection media. This density was determined to provide for a high probability of single clones in any well showing growth in the plates. Approximately 12 to 14 days later growth was sufficient for screening.

Example 25

Hybridoma Screening

Wells showing sufficient growth were tested by drawing off 160 μl of culture media under aseptic conditions. This aliquot was divided into three parts of 50 μl each. Aliquots were placed in wells previously coated with LSD-BSA, 2-oxo-3-hydroxy-LSD-BSA, or nor-LSD-BSA and incubated for 1 hour at 37° C. After incubation, the wells were washed with phosphate buffered saline (PBS)-TWEEN-20 emulsifying agent solution, and 50 μl of a preoptimized dilution of goat anti-mouse IgG antibody conjugated to horseradish peroxidase (HRP, Zymed, San Diego, Calif.) was added to each well. The plates were again incubated for 1 hour at 37° C. The plates were extensively washed after incubation and 100 μl of an enzyme substrate solution (K-BLUE, Neogen Corp, Lexington Ky.) was added. Color was allowed to develop for 15 minutes in the dark before the reaction was stopped by the addition of 100 μl of 2M phosphoric acid. Optical density was read at 450 nanometers.

The optical density of the reactions on the three substrates was collated for each well tested. In this manner it was possible to rapidly estimate the cross specificity of each monoclonal antibody. The data were collated by means of a computer program designed for this purpose. A critical point is to be assured that the growth of cells in any well tested is due solely to a single clone. This was an important feature as multiple clones per well could result in false cross reactivity profiles. The screening protocol used, therefore, in this work consisted of predilution of the fusion cell mixture to a point to provide statistical evidence that monoclonal growth was actually obtained. This was followed with a screening method consisting of all three drug-BSA conjugates separately but at the same time.

The results were that sixteen clones showed essentially equivalent reactions to both LSD and 2-oxo-3-hydroxy-LSD. Additionally, seven showed equivalent reactions to both LSD, 2-oxo-3-hydroxy-LSD and significant reaction to nor-LSD. These 23 clones were chosen for further work which consisted of limiting dilution subcloning to assure stability of antibody production, expansion cultures to provide cells for storage in liquid nitrogen freezers, and larger quantities of antibody containing media for use in establishing the exact cross reactivity profiles.

Subsequent cross reactivity studies with the stabilized clone derived antibodies showed essentially the same profiles as was estimated by the fusion screening.

Example 26

Antibody Cross-reactivity

Cross-reactivity of three clones for LSD, nor-LSD and 2-oxo-3-hydroxy-LSD was determined using an ELISA technique. Microtiter plates were coated with 100 μl of 0.325 mg/ml LSD-BSA or 100 μl of 0.325 mg/ml 2-oxo-3-hydroxy-LSD-BSA for 1 hour at 37° C. and post-blocked with 200 μl of 1% BSA in PBS for 1 hour at room temperature. Plates were washed 3 times with 400 μl of PBS-0.1% TWEEN-20. Free LSD, nor-LSD and 2-oxo-3-hydroxy-LSD were diluted to 1000 ng/ml in PBS. Antibody was diluted 8,000 fold. Drug solutions, 200 μl of 1000 ng/ml, solutions were dispensed into the first column of an ELISA plate. The rest of the wells were filled with 100 μl of PBS. Serial dilutions of the drugs were prepared by taking 100 μl of the drug solution out of the first column and dispensing it into the second column of the plate. Contents of the wells were mixed thoroughly by pipetting the solution up and down 5 times. 100 μl out of the second column was dispensed into the third column and mixed as above. The process was repeated for all 12 columns of ELISA plates.

100 μl of solution out of the last wells was discarded. 100 μl of antibody diluted 8,000 fold was added to each well. Resulting concentrations of the drug were 500 ng/ml, 250 ng/ml, 125 ng/ml, 62.5 ng/ml, 31.2 ng/ml, 15.6 ng/ml, 7.81 ng/ml, 3.90 ng/ml, 1.95 ng/ml, 0.976 ng/ml, 0.488 ng/ml, 0.244 ng/ml. Final antibody dilution was 16,000 fold. Plates were incubated for 1 hour at 37° C. and washed 3 times with PBS-TWEEN-20. Rabbit anti-mouse HRP conjugated IgG was diluted 5,000 fold and 100 μl were added to ELISA plates. The plates were incubated for 1 hour at 37° C. and washed 3 times with PBS-TWEEN-20. 100 μl of K-BLUE substrate was dispensed into each well. Plates were incubated for 30 min at room temperature in the dark. The reaction was stopped with 100 μl of 2 M $H_3PO_4$, and absorbance was read at 450 nm. Results for the three clones were as follows:

| Dilution | $A_{450}$ LSD wells | $A_{450}$ nor-LSD wells | $A_{450}$ 2-oxo-3-hydroxy-LSD wells |
|---|---|---|---|
| Clone 1.1: | | | |
| 0.2 | 3.797 | 4.019 | 3.913 |
| 0.5 | 4.085 | 4.074 | 3.928 |
| 1.0 | 3.962 | 4.100 | 4.033 |
| 2.0 | 3.905 | 3.884 | 4.015 |
| 3.9 | 3.951 | 4.035 | 3.908 |
| 7.8 | 3.831 | 3.805 | 3.914 |
| 15.6 | 3.519 | 3.740 | 3.310 |
| 31.3 | 3.390 | 3.735 | 3.108 |
| 62.5 | 2.633 | 3.601 | 2.278 |
| 125.0 | 2.050 | 3.512 | 1.768 |
| 250.0 | 1.433 | 3.340 | 1.425 |
| 500.0 | 0.831 | 2.968 | 0.871 |
| Clone 2.1: | | | |
| 0.2 | 0.831 | 0.900 | 0.846 |
| 0.5 | 0.738 | 0.859 | 0.690 |
| 1.0 | 0.579 | 0.842 | 0.552 |
| 2.0 | 0.523 | 0.792 | 0.531 |
| 3.9 | 0.435 | 0.786 | 0.372 |
| 7.8 | 0.339 | 0.696 | 0.321 |
| 15.6 | 0.303 | 0.648 | 0.294 |
| 31.3 | 0.294 | 0.504 | 0.309 |
| 62.5 | 0.252 | 0.444 | 0.243 |
| 125.0 | 0.240 | 0.384 | 0.256 |
| 250.0 | 0.234 | 0.318 | 0.297 |
| 500.0 | 0.236 | 0.276 | 0.243 |
| Clone 20.2: | | | |
| 0.2 | 0.833 | 0.908 | 0.838 |
| 0.5 | 0.658 | 0.866 | 0.704 |
| 1.0 | 0.587 | 0.853 | 0.430 |
| 2.0 | 0.328 | 0.799 | 0.372 |
| 3.9 | 0.284 | 0.722 | 0.316 |
| 7.8 | 0.204 | 0.656 | 0.272 |
| 15.6 | 0.160 | 0.584 | 0.220 |
| 31.3 | 0.126 | 0.464 | 0.148 |
| 62.5 | 0.126 | 0.416 | 0.142 |
| 125.0 | 0.124 | 0.292 | 0.143 |
| 250.0 | 0.188 | 0.228 | 0.144 |
| 500.0 | 0.122 | 0.288 | 0.142 |

Calculated percentage cross-reactivity for the three clones based upon specificity to 2-oxo-3-hydroxy-LSD was as follows:

| | Clone 1.1 | Clone 2.1 | Clone 20.2 |
|---|---|---|---|
| LSD | 74.9% | 76.1% | 84.4% |
| nor-LSD | 1.9 | 1.8 | 4.6 |
| 2-oxo-3-hydroxy-LSD | 100.0 | 100.0 | 100.0 |

Calculated percentage cross-reactivity for the three clones based upon specificity to LSD was as follows:

| | Clone 1.1 | Clone 2.1 | Clone 20.2 |
|---|---|---|---|
| LSD | 100.0% | 100.0% | 100.0% |
| nor-LSD | 2.6 | 2.3 | 5.5 |
| 2-oxo-3-hydroxy-LSD | 133.6 | 131.4 | 118.5 |

Example 27

Preparation of Aminodextran Conjugate (XVII)

To a three-necked 3 liter round-bottom flask equipped with a mechanical stirrer was added 700 ml of deionized water. 70 g (1.86 mmol) of dextran (Sigma, MW 37,500) was added portionwise to the reaction flask while stirring and dissolving the dextran in water at room temperature. To the reaction mixture 140 ml of 1 N NaOH was added, and the reaction was heated to 30–35° C. To the reaction mixture, a solution of 79 ml (923 mmol) of epibromohydrin in 245 ml of 1,4-dioxane was added dropwise over a period of 45 minutes at 30–35° C. The resulting reaction mixture was stirred and heated at 30–35° C. for an additional 4 hours. The reaction mixture was allowed to cool to room temperature and transferred to a 2 liter separatory funnel. The organic layer slowly separated as a bottom layer and was discarded until no significant build up was noticed. The aqueous solution was transferred into a 3 liter round bottom flask and cooled in an ice-water bath. A solution of 700 ml of 25% ammonium hydroxide was added to the reaction flask and the pH was adjusted to 11 with 1 N HCl. The resulting solution was allowed to warm to room temperature overnight. The reaction solution was transferred to 20 pieces of dialysis tubing with MWCO of 2,000 daltons, and the dialysis was conducted in two 12 liter buckets according to the following schedule of changes: 1% acetic acid for 6 hours, 1% acetic acid for 24 hours, 1% acetic acid for 48 hours, and deionized water for 24 hours×6 (volumes=20 liters).

The dialyzed solution was first concentrated in a rotary evaporator and then lyophilized to give 48 g of product as a white solid. By using TNBS assay (Goldfarb, A. R., *Biochem.* 5, 2570–2574, 1966 and Snyder, S. L. et al., *Anal. Biachem.* 64, 284–288, 1975), the product was found to contain 5.7 amino groups for every mole of aminodextran.

The aminodextran conjugate was prepared as follows. To a stirred solution of aminodextran (236 mg, 0.0063 mmol) in 25 ml of DMSO was added 2-oxo-3-hydroxy-LSD NHS ester XII (36.7 mg, 0.05 mmol) in 1 ml of anhydrous DMF followed by triethylamine (0.008 ml, 0.058 mmol) at room temperature. The solution was stirred at room temperature overnight. The solution was transferred to dialysis bags (2000 MW cut off) and dialyzed against 2 liters of the following: 80% DMSO in deionized water for 4 hours, 60% DMSO in deionized water for 4 hours, 40% DMSO in deionized overnight, 20% DMSO in deionized water for 4 hours, deionized water overnight, deionized water for 4 hours, and deionized water overnight. The solution in the bag was lyophilized overnight to afford 225 mg of product as white foam.

Example 28

Assay for LSD

A first working reagent was prepared by making a 0.175 M PIPES buffer, pH 7.0, containing 0.1% BSA and 0.1% sodium azide. To this was added 2-oxo-3-hydroxy-LSD-aminodextran conjugate to give a concentration of 50 ng/ml. To this was also added polyacrylic acid to give a concentration of 1.4%.

A second working reagent was prepared by making a 0.05 M MOPS buffer, pH 7.2, containing 0.09% sodium azide and 0.1% BSA.

To prepare the microparticles, equal volumes of a 1% microparticle solution and a 15 µg/ml antibody solution in a 0.05 M MES buffer, pH 6.5, containing 0.09% sodium azide were combined and incubated overnight. The microparticles were then washed with a 0.01 M phosphate buffered saline solution, pH 7.4, containing 0.09% sodium azide and 0.05% BSA.

A microparticle reagent was prepared by diluting microparticles with the second working reagent to give a particle concentration of 0.15%. The antibody used was from the clone designated 2.1 and the load on the microparticles was about 15 µg/ml.

Calibrators were prepared by first making a stock solution of LSD at a concentration of 1000 ng/ml in urine. From this stock solution, dilutions in urine were made to generate solutions having LSD concentrations of 0.5, 1.0, 2.0, 5.0 and 10 ng/ml.

Figure 7:
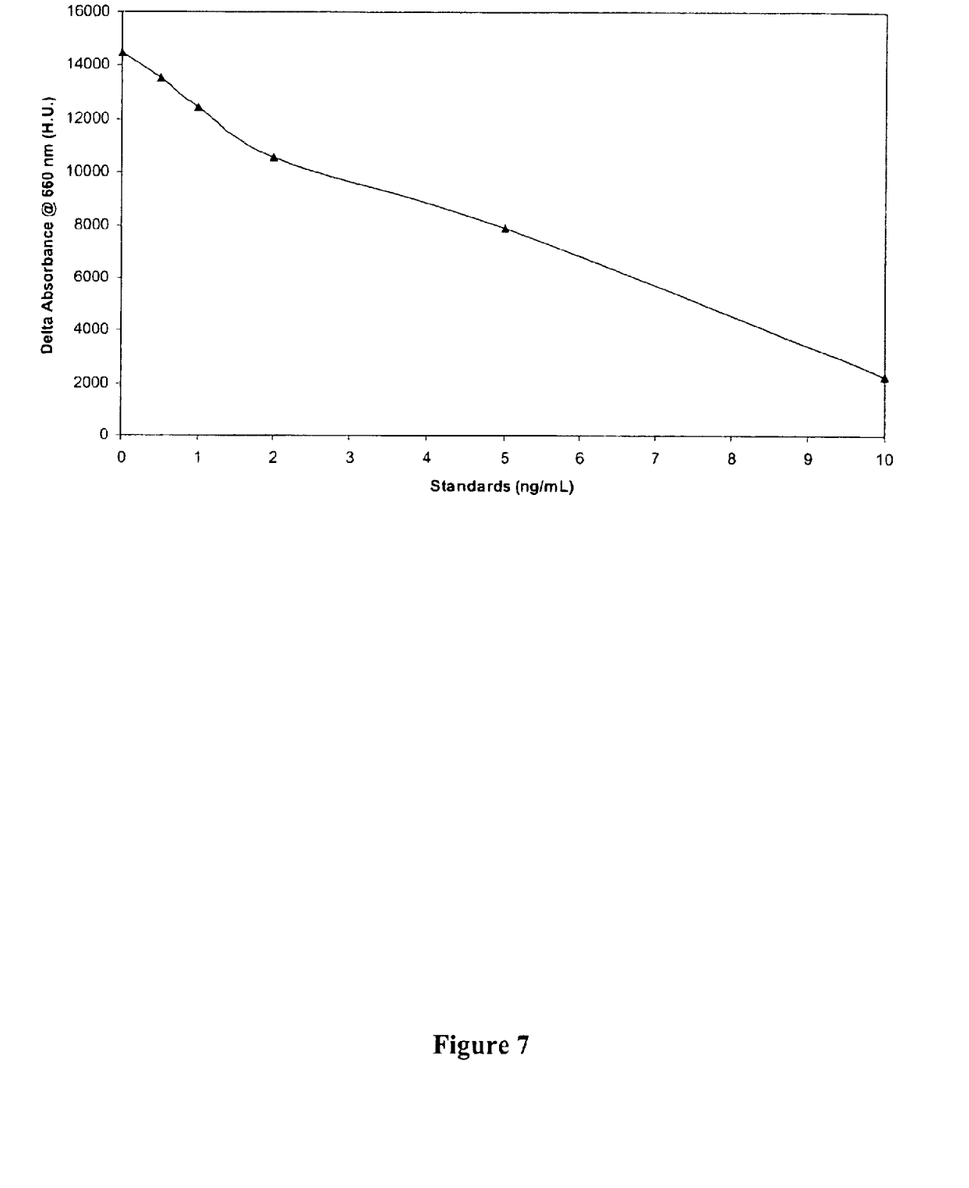
FIG. 7 is a calibration (dose response) curve generated as described in Example 28. Concentration of LSD is plotted on the X-axis and absorbance at 660 nm is plotted on the Y-axis.

An assay was performed using an Hitachi 917 automated analyzer (Roche Diagnostics Corporation, Indianapolis) using a 19 µl sample volume, 180 µl of the first working reagent and 80 µl of the second working reagent. Results are shown in FIG. 7, where HU is the abbreviation for Hitachi units (10,000 Hitachi units=1 absorbance unit=1 OD).

The invention now being fully described, it will be understood that the specification and examples are illustrative but not limiting of the present invention, and that modifications and changes will suggest themselves to those skilled in the art but will not depart from the spirit and scope of the appended claims.

What is claimed is:

1. A compound having the formula wherein:
$R_1$ and $R_2$ are independently selected from the group consisting of H and $CON(CH_2CH_3)_2$, provided that at least one of $R_1$ and $R_2$ is H,
$R_3$ is H,
$R_4$ is a branched or straight chain linking group having 1–10 carbon atoms with 0–2 unsaturated bonds and 0–6 heteroatoms, and
$R_5$ is selected from the group consisting of $COR_6$ and $NHR_7$, wherein $R_6$ is OH, L or LX and wherein $R_7$ is H, L or LX, L is a linking group and X is a detector or carrier molecule bound through L.

2. The compound of claim 1, wherein $R_1$ is $CON(CH_2CH_3)_2$ and $R_2$ is H.

3. The compound of claim 2, wherein $R_5$ is $COR_6$ and $R_6$ is OH.

4. The compound of claim 2, wherein $R_5$ is $NHR_7$ and $R_7$ is H.

5. The compound of claim 2, wherein $R_5$ is $NHR_7$ and $R_7$ is a linking group L selected from the group consisting of where Z is selected from the group consisting of COOH, SCN and N-hydroxysuccinimide ester.

6. The compound of claim 2, wherein $R_5$ is $NHR_7$, $R_7$ is LX and X is a carrier molecule selected from the group consisting of bovine thyroglobulin, keyhole limpet hemocyanin and bovine serum albumin.

7. The compound of claim 2, wherein $R_5$ is $NHR_7$, $R_7$ is LX and X is a detector molecule.

8. The compound of claim 1, wherein $R_1$ is $CON(CH_2CH_3)_2$, $R_2$ is H, $R_4$ is $(CH_2)_3$, $R_5$ is $NHR_7$ and $R_7$ is a linking group L selected from the group consisting of where Z is selected from the group consisting of COOH, NCS and N-hydroxysuccinimide ester.

9. The compound of claim 1, wherein $R_1$ is $CON(CH_2CH_3)_2$, $R_2$ is H, $R_4$ is $(CH_2)_3$, $R_5$ is $NHR_7$ and $R_7$ is LX wherein LX is L selected from the group consisting of wherein X is a detector or a carrier molecule.

10. The compound of claim 9, wherein X is a carrier molecule selected from the group consisting of bovine thyroglobulin, keyhole limpet hemocyanin and bovine serum albumin.

* * * * *